US009971874B2

(12) United States Patent
Jafari et al.

(10) Patent No.: US 9,971,874 B2
(45) Date of Patent: May 15, 2018

(54) WEARABLE MEDICATION ADHERENCE MONITORING

(71) Applicants: Roozbeh Jafari, Dallas, TX (US); Nasser Kehtarnavaz, Frisco, TX (US); Chen Chen, Richardson, TX (US)

(72) Inventors: Roozbeh Jafari, Dallas, TX (US); Nasser Kehtarnavaz, Frisco, TX (US); Chen Chen, Richardson, TX (US)

( * ) Notice: Subject to any disclaimer, the term of this patent is extended or adjusted under 35 U.S.C. 154(b) by 246 days.

(21) Appl. No.: 14/834,326

(22) Filed: Aug. 24, 2015

(65) Prior Publication Data

US 2016/0055316 A1  Feb. 25, 2016

Related U.S. Application Data

(60) Provisional application No. 62/040,531, filed on Aug. 22, 2014.

(51) Int. Cl.
  *G08B 23/00* (2006.01)
  *G06F 19/00* (2018.01)
  *G08B 21/24* (2006.01)
  *A61J 7/04* (2006.01)

(52) U.S. Cl.
  CPC ......... *G06F 19/3456* (2013.01); *G08B 21/24* (2013.01); *A61J 7/0409* (2013.01); *A61J 2200/30* (2013.01)

(58) Field of Classification Search
  CPC ..... A61B 5/0006; A61B 5/721; A61B 5/0002; A61B 5/0008; A61B 5/7221; A61B 5/1124; G06F 19/323; G06F 19/3456; G08B 21/24

USPC ...... 340/573.1, 539.12, 572.1; 600/595, 301, 600/484, 300, 479
See application file for complete search history.

(56) References Cited

U.S. PATENT DOCUMENTS

| | | | | |
|---|---|---|---|---|
| 4,836,778 A | * | 6/1989 | Baumrind | A61C 19/045 |
| | | | | 356/139.03 |
| 8,040,236 B2 | * | 10/2011 | Larsen | G06F 19/3418 |
| | | | | 340/309.16 |
| 9,204,806 B2 | * | 12/2015 | Stivoric | A61B 5/0008 |
| 9,847,012 B2 | * | 12/2017 | Zomet | G06F 19/3456 |
| 2005/0240086 A1 | * | 10/2005 | Akay | A61B 5/0002 |
| | | | | 600/300 |
| 2006/0161079 A1 | * | 7/2006 | Choi | A61B 5/1117 |
| | | | | 600/595 |

(Continued)

*Primary Examiner* — Hoi Lau
(74) *Attorney, Agent, or Firm* — NovoTechIP International PLLC

(57) ABSTRACT

A method including obtaining a first motion signal segment sensed by a motion sensor worn on a user's wrist or forearm; detecting the user performed a first action based on the first motion signal segment; obtaining a second motion signal segment sensed by the motion sensor, wherein the second motion signal segment was sensed by the motion sensor after the first motion signal segment; detecting the user performed a second action based on the second motion signal segment and in response to the detection of the first action; determining that a first medication was taken by the user based on the detection of the second action; and, in response to the determination that the first medication was taken by the user, causing presentation of an indication to the user or transmitting an indication to an external device that the first medication was taken by the user.

28 Claims, 9 Drawing Sheets

(56) References Cited

U.S. PATENT DOCUMENTS

| | | | | |
|---|---|---|---|---|
| 2008/0276461 A1* | 11/2008 | Gold | ...................... | A47G 21/02 |
| | | | | 30/142 |
| 2008/0294019 A1* | 11/2008 | Tran | ..................... | A61B 5/0006 |
| | | | | 600/301 |
| 2009/0322533 A1* | 12/2009 | Bomba | .............. | G08B 21/0446 |
| | | | | 340/572.1 |
| 2011/0276312 A1* | 11/2011 | Shalon | .................... | A61B 5/11 |
| | | | | 702/187 |
| 2013/0267794 A1* | 10/2013 | Fernstrom | .............. | G01N 33/02 |
| | | | | 600/301 |
| 2013/0336519 A1* | 12/2013 | Connor | .............. | G06K 9/00771 |
| | | | | 382/100 |
| 2014/0099614 A1* | 4/2014 | Hu | ........................ | G09B 19/00 |
| | | | | 434/236 |
| 2014/0180136 A1* | 6/2014 | Su | ........................ | A61B 5/7221 |
| | | | | 600/479 |
| 2014/0257141 A1* | 9/2014 | Giuffrida | ............. | A61B 5/1124 |
| | | | | 600/595 |
| 2014/0315170 A1* | 10/2014 | Ionescu | ............... | G06F 19/3456 |
| | | | | 434/236 |
| 2014/0377724 A1* | 12/2014 | Hoover | .............. | G09B 19/0092 |
| | | | | 434/127 |
| 2015/0168365 A1* | 6/2015 | Connor | .................. | G01N 33/02 |
| | | | | 356/51 |
| 2015/0198460 A1* | 7/2015 | Yamato | ................ | A61B 5/1118 |
| | | | | 702/160 |
| 2015/0230756 A1* | 8/2015 | Luna | ...................... | A61B 5/721 |
| | | | | 600/484 |
| 2015/0238139 A1* | 8/2015 | Raskin | ................ | A61B 5/4866 |
| | | | | 600/595 |
| 2015/0269825 A1* | 9/2015 | Tran | ................... | G08B 21/0446 |
| | | | | 340/539.12 |
| 2016/0005299 A1* | 1/2016 | Zomet | ................ | G06F 19/3456 |
| | | | | 340/573.1 |
| 2016/0055316 A1* | 2/2016 | Jafari | ................. | G06F 19/3456 |
| | | | | 340/573.1 |
| 2016/0284200 A1* | 9/2016 | Song | ................... | G06F 3/03546 |
| 2016/0306932 A1* | 10/2016 | Fateh | .................... | G06F 19/323 |

\* cited by examiner

WEARABLE MEDICATION ADHERENCE MONITORING

CROSS REFERENCE TO RELATED APPLICATION

This application claims the benefit of priority from U.S. Provisional Patent Application Ser. No. 62/040,531, filed on Aug. 22, 2014, and entitled "Wearable Medication Adherence Monitoring," which is incorporated by reference herein in its entirety.

BACKGROUND

Adherence to medication regimens continues to rank as a major clinical problem in disease management. Achieving optimal medication adherence requires patients being prescribed the right medication, filling it and taking it correctly over time. This requires appropriate prescribing, effective patient-provider communication, coordination among care-providers and active engagement and participation by patients. Poor adherence to medication regimens accounts for a substantial load on health care costs in the United States. Of all medication-related hospital admissions in the United States, 33 to 69 percent are due to poor medication adherence, costing more than $100 billion annually in increased medical costs.

There have been a number of efforts addressing systems or devices for medication adherence. For example, a context-aware pill bottle/stand that provided visual and audio alerts to take a medication on time was developed in A. Agarawala, S. Greenberg, and G. Ho, "The context-aware pill bottle and medication monitor," Technical Report, Department of Computer Science, University of Calgary, Calgary, Canada, 2004. The system operated based on the limiting assumption that the pill was taken when a pill bottle was removed from the stand. A smart medication dispenser was proposed in J. Pak and K. Park, "Construction of a smart medication dispenser with high degree of scalability and remote manageability," Journal of Biomedicine and Biotechnology, vol. 2012, 2012, which dispensed a predetermined medication at a predetermined time. Again, this device did not detect whether the user was actually taking the medication. Methods based on computer vision techniques have also appeared in H. H. Huynh, J. Meunier, J. Sequeira, and M. Daniel, "Real time detection, tracking and recognition of medication intake," World Academy of Science, Engineering and Technology, vol. 60, pp. 280-287, 2009; G. Bilodeau and S. Ammouri, "Monitoring of medication intake using a camera system," Journal of Medical Systems, vol. 35, no. 3, pp. 377-389, 2011; and F. Hasanuzzaman, X. Yang, Y. Tian, Q. Liu, and E. Capezuti, "Monitoring activity of taking medicine by incorporating RFID and video analysis," Network Modeling Analysis in Health Informatics and Bioinformatics, pp. 1-10, 2013. Obviously, the limitation with such vision based systems is that they require the user to take a medication within the field of view of a camera and cannot monitor the user wherever the user goes. A system consisting of several sensors (motion sensor, wearable sensor and bed sensor) was proposed in J. Lundell, T. L. Hayes, S. Vurgun, U. Ozertem, J. Kimel, J. Kaye, F. Guilak, and M. Pavel, "Continuous activity monitoring and intelligent contextual prompting to improve medication adherence," IEEE Proceedings of 29th Annual International Conference on Engineering in Medicine and Biology Society (EMBS), pp. 6286-6289, 2007, which was rather complex to set up and operate. Each of the above-noted papers is hereby incorporated by reference in their entireties.

The availability of a low-cost and easy-to-use device for monitoring medication adherence has been lacking. This disclosure generally relates to wearable medication adherence monitoring systems and methods.

SUMMARY

In a general aspect, method comprising obtaining a first motion signal segment sensed by a motion sensor worn on a user's wrist or forearm; detecting the user performed a first action based on the first motion signal segment; obtaining a second motion signal segment sensed by the motion sensor, wherein the second motion signal segment was sensed by the motion sensor after the first motion signal segment; detecting the user performed a second action based on the second motion signal segment and in response to the detection of the first action; determining that a first medication was taken by the user based on the detection of the second action; and in response to the determination that the first medication was taken by the user, causing presentation of an indication to the user or transmitting an indication to an external device that the first medication was taken by the user.

Particular implementations may include one or more of the following features. In response to the detection of the first action based on the first motion signal segment, the method may initiate a time period to begin at a time associated with the sensing of the first motion signal segment, wherein the determination that the first medication was taken by the user is further based on a time associated with the sensing of the second motion signal segment having occurred within a predetermined amount of time after the beginning of the time period.

The method may also include obtaining a third motion signal segment sensed by the motion sensor, wherein the third motion signal segment was sensed by the motion sensor after the first motion signal segment; detecting the user performed the first action based on the third motion signal segment; and in response to the detection of the first action based on the third motion signal segment, reinitiating the time period to begin at a time associated with the sensing of the third motion signal segment.

The first and second motion signal segments may indicate acceleration of the motion sensor along an axis substantially parallel to a longitudinal direction of the user's forearm.

The method may also include identifying a first segment of motion signals sensed by the motion sensor as the first motion signal segment in response to the first segment of motion signals matching a first user-specific template signal generated based on a third motion signal segment sensed by the motion sensor while the user performed the first action at a first time; and identifying a second segment of motion signals sensed by the motion sensor as the second motion signal segment in response to the second segment of motion signals matching a second user-specific template signal generated based a fourth motion signal segment sensed by the motion sensor while the user performed the second action at a second time.

The method may also include obtaining a fifth motion signal segment sensed by the motion sensor, wherein the fifth motion signal segment was sensed by the motion sensor after the second motion signal segment; detecting the user performed the first action based on the fifth motion signal segment; and revising or replacing the first template signal or adding a new template signal based on the first motion signal segment and the fifth motion signal segment.

The method may also include calculating a confidence level that the first motion signal segment matches the first template signal; in response to the detection of the second action and the confidence level, causing presentation of a request for confirmation that the first medication was taken; obtaining a first response to the request indicating that the first medication was taken; and in response to the first response indicating the first medication was taken, revising the first template signal based on the first motion signal segment or generating a third template signal based on the first motion signal segment, wherein the determination that the first medication was taken by the user is further based on the first response.

The method may also include obtaining a third user-specific template signal generated based on a motion signal segment sensed by the motion sensor while the user performed the first action, wherein the detection of the first action includes determining whether the first motion signal segment matches the third template signal.

The method may also include tracking positions of the user's left and right wrists using a camera and capturing motion signals sensed by the motion sensor while the user sequentially performs the first action at the first time and then the second action at the second time; automatically determining a start and an end of the user's performance of the first action at the first time based on the tracked positions; automatically determining a start and an end of the user's performance of the second action at the second time based on the tracked positions; automatically identifying the third motion signal segment from the captured motion signals based on the determined start and end of the user's performance of the first action at the first time; and automatically identifying the fourth motion signal segment from the captured motion signals based on the determined start and end of the user's performance of the second action at the second time.

The first action may comprise the user opening a container containing the first medication; and the second action may comprise the user moving a hand to the user's mouth.

The container may be a twist-cap prescription bottle, a foil wrapping, a syrup container, or a cream tube.

The method may also include obtaining an indication that the user is in proximity to an RFID tag attached to a container containing the first medication, wherein the determination that the first medication was taken by the user is further based on the indication.

The method may also include obtaining a proximity signal indicating that the user is in proximity to a container containing the first medication, the proximity signal including an identification of the container or a content of the container, wherein the determination that the first medication was taken by the user is further based on the proximity signal.

The method may also include alerting the user with an audible or visible signal to take the first medication at a first time, wherein the determination that the first medication was taken by the user is further based on the first motion signal segment or the second motion signal segment having been sensed within a predetermined period of time after the first time.

The method may also include obtaining a third motion signal segment sensed by the motion sensor, wherein the third motion signal segment was sensed by the motion sensor after the second motion signal segment; detecting the user performed the first action based on the third motion signal segment; obtaining a fourth motion signal segment sensed by the motion sensor, wherein the fourth motion signal segment was sensed by the motion sensor after the third motion signal segment; detecting the user performed the second action based on the fourth motion signal segment; and issuing an alert in response to a time associated with the sensing of the fourth motion signal segment occurring within a predetermined amount of time of a time associated with the sensing of the second motion signal segment.

The method may also include, in response to the determination that the first medication was taken by the user, scheduling a reminder for the user to take the first medication.

In a general aspect, a system for medication adherence monitoring, the system comprising: a housing configured to be worn on a user's wrist or forearm; a motion sensor mounted within the housing; one or more processors each configured to execute instructions; and one or more non-transitory storage mediums configured to provide stored instructions to the one or more processors which cause the one or more processors to: obtain a first motion signal segment sensed by the motion sensor; detect the user performed a first action based on the first motion signal segment; obtain a second motion signal segment sensed by the motion sensor, wherein the second motion signal segment was sensed by the motion sensor after the first motion signal segment; detect the user performed a second action based on the second motion signal segment and in response to the detection of the first action; determine that a first medication was taken by the user based on the detection of the second action; and cause presentation of an indication to the user or transmit an indication to an external device that the first medication was taken by the user in response to the determination that the first medication was taken by the user.

Particular implementations may include one or more of the following features. The motion sensor may include an accelerometer configured with an axis for measuring acceleration that is substantially parallel to a longitudinal direction of the user's forearm when the housing is worn on the user's wrist or forearm.

The one or more processors may be mounted in the housing.

The stored instructions may further cause the one or more processors to identify a first segment of motion signals sensed by the motion sensor as the first motion signal segment in response to the first segment of motion signals matching a first user-specific template signal generated based on a third motion signal segment sensed by the motion sensor while the user performed the first action at a first time; and identify a second segment of motion signals sensed by the motion sensor as the second motion signal segment in response to the second segment of motion signals matching a second user-specific template signal generated based a fourth motion signal segment sensed by the motion sensor while the user performed the second action at a second time.

The system may also include an RFID reader configured to generate a proximity signal indicating that the RFID reader is in proximity to an RFID tag attached to a container containing the first medication, wherein the stored instructions further cause the one or more processors to make the determination that the first medication was taken by the user further based on the proximity signal.

The system may also include a proximity detector configured to generate a proximity signal in response to the proximity detector being in proximity to a container containing the first medication, the proximity signal including an identification of the container or a content of the container, wherein the stored instructions further cause the one or more processors to make the determination that the first medication was taken by the user further based on the proximity signal.

In a general aspect, a nontransitory computer readable storage medium comprising a plurality of instructions which when executed by one or more processors, cause the one or more processors to: obtain a first motion signal segment sensed by a motion sensor worn on a user's wrist or forearm; detect the user performed a first action based on the first motion signal segment; obtain a second motion signal segment sensed by the motion sensor, wherein the second motion signal segment was sensed by the motion sensor after the first motion signal segment; detect the user performed a second action based on the second motion signal segment and in response to the detection of the first action; determine that a first medication was taken by the user based on the detection of the second action; and in response to the determination that the first medication was taken by the user, cause presentation of an indication to the user or transmitting an indication to an external device that the first medication was taken by the user.

Particular implementations may include one or more of the following features. The instructions may further cause the one or more processors to: initiate a time period to begin at a time associated with the sensing of the first motion signal segment, in response to the detection of the first action based on the first motion signal segment; and make the determination that the first medication was taken by the user further based on a time associated with the sensing of the second motion signal segment having occurred within a predetermined amount of time after the beginning of the time period.

The instructions may further cause the one or more processors to: identify a first segment of motion signals sensed by the motion sensor as the first motion signal segment in response to the first segment of motion signals matching a first user-specific template signal generated based on a third motion signal segment sensed by the motion sensor while the user performed the first action at a first time; and identify a second segment of motion signals sensed by the motion sensor as the second motion signal segment in response to the second segment of motion signals matching a second user-specific template signal generated based a fourth motion signal segment sensed by the motion sensor while the user performed the second action at a second time.

The instructions may further cause the one or more processors to: calculate a confidence level that the first motion signal segment matches the first template signal; in response to the detection of the second action and the confidence level, cause presentation of a request for confirmation that the first medication was taken; obtain a first response to the request indicating that the first medication was taken; in response to the first response, revise the first template signal based on the first motion signal segment or generate a third template signal based on the first motion signal segment; and make the determination that the first medication was taken by the user further based on the first response.

The instructions may further cause the one or more processors to: obtain an indication that the user is in proximity to an RFID tag attached to a container containing the first medication; and make the determination that the first medication was taken by the user further based on the indication.

The instructions may further cause the one or more processors to: obtain a proximity signal indicating that the user is in proximity to a container containing the first medication, the proximity signal including an identification of the container or a content of the container; and make the determination that the first medication was taken by the user further based on the proximity signal.

Other features and aspects will be apparent from the following detailed description, the drawings, and the claims.

DETAILED DESCRIPTION

The following detailed descriptions are presented to enable any person skilled in the art to make and use the disclosed subject matter. For purposes of explanation, specific nomenclature is set forth to provide a thorough understanding. However, it will be apparent to one skilled in the art that these specific details are not required to practice the disclosed subject matter. Descriptions of specific applications are provided only as representative examples. Various modifications to the preferred embodiments will be readily apparent to one skilled in the art, and the general principles defined herein may be applied to other embodiments and applications without departing from the scope of this disclosure. The sequences of operations described herein are merely examples, and the sequences of operations are not limited to those set forth herein, but may be changed as will be apparent to one of ordinary skill in the art, with the exception of operations necessarily occurring in a certain order. Also, description of functions and constructions that are well known to one of ordinary skill in the art may be omitted for increased clarity and conciseness. This disclosure is not intended to be limited to the embodiments shown, but is to be accorded the widest possible scope consistent with the principles and features disclosed herein.

Figure 1:
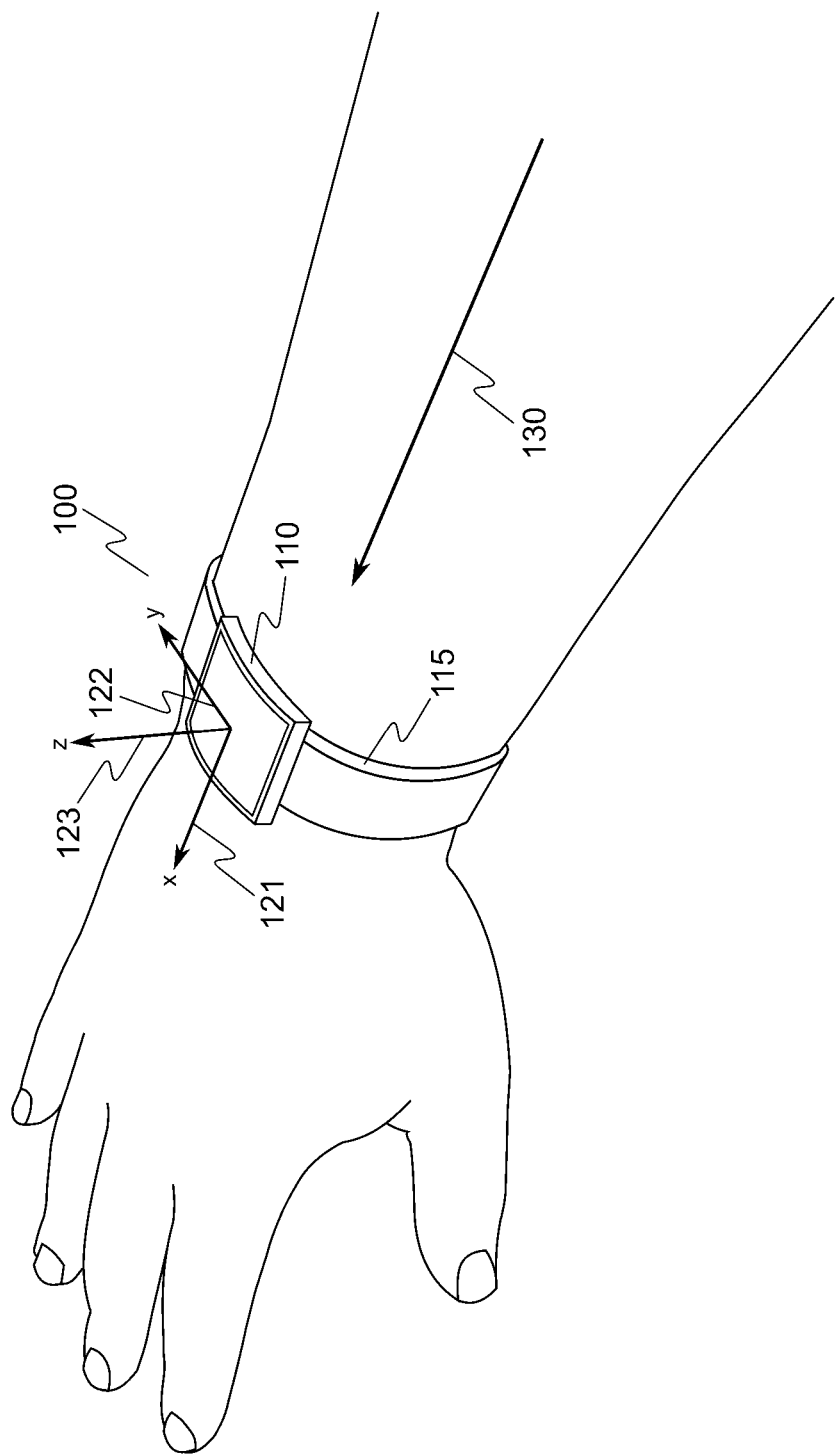
FIG. 1 illustrates an example of a motion sensing device 100 being worn on an arm of a user.

FIG. 1 illustrates an example of a motion sensing device 100 being worn on an arm of a user. Motion sensing device 100 includes a housing 110 which is configured to be worn on a user's wrist or forearm. Housing 110 may include strap 115. In the particular example illustrated in FIG. 1, housing 100 is in a watch-like form factor configured to be worn on or near a user's wrist. However, the housing 100 may not be limited to the illustrated watch-like form factor and may take other form factors instead.

In some examples, it is preferred for the user to wear motion sensing device 100 on their dominant hand (for example, the user's right hand, if the user is right-handed, or the user's left hand, if the user is left-handed). The desired hand for wearing motion sensing device 100 may depend on actions to be detected by motion sensing device 100. For example, if a hand to mouth action, such as for consuming a pill, is of interest, motion sensing device 100 should be worn on the hand the user generally uses for the action of interest, such as the user's dominant hand, to improve the likelihood of detecting the action of interest.

Motion sensing device 100 includes a motion sensor (not illustrated in FIG. 1) mounted within housing 110. Motion sensor allows motion signals to be obtained, which provide information about movement of motion sensing device 100. In some examples, the motion sensor includes one or more accelerometers, such as, but not limited to, MEMS-based accelerometers. In some examples, the motion sensor includes an accelerometer configured with an axis for measuring acceleration along x-axis 121, which is substantially parallel to a longitudinal direction 130 of a user's forearm when motion sensing device 100 is worn on the user's wrist or forearm, as illustrated, for example, in FIG. 1. In some examples, the motion sensor includes an accelerometer configured with an axis for measuring acceleration along y-axis 122. In some examples, the motion sensor includes an accelerometer configured with an axis for measuring acceleration along z-axis 123. In some examples, as illustrated in FIG. 1, z-axis 123 is approximately normal to an outer surface of housing 110. In some examples, x-axis 121, y-axis 122, and/or z-axis 123 may be oriented differently than illustrated in FIG. 1. In FIG. 1, x-axis 121, y-axis 122, and z-axis 123 are orthogonal to each other. In some examples, acceleration along a virtual axis other than x-axis 121, y-axis 122, or z-axis 123 may be determined based on acceleration measured on two or more of x-axis 121, y-axis 122, and z-axis 123.

In some examples, the motion sensor includes one or more gyroscopes, such as, but not limited to, MEMS-based gyroscopes. For example, motion sensor may include three gyroscopes, with a first gyroscope configured to measure rotation about x-axis 121, a second gyroscope configured to measure rotation about y-axis 122, and a third gyroscope configured to measure rotation about z-axis 123. In some examples, rotation about a virtual axis other than x-axis 121, y-axis 122, or z-axis 123 may be determined based on rotation measured on two or more of x-axis 121, y-axis 122, and z-axis 123.

In some examples, the motion sensor may measure and/or be used to determine motion of motion sensing device 100 using a non-accelerometer-, non-gyroscope-based sensor. For example, the motion sensor may include one or more optical sensors, such as, but not limited to cameras, to determine motion of motion sensing device 100.

In some examples, the motion sensor may be capable of measuring movement in more than one degree of freedom (DOF). For example, motion sensor may have six degrees of freedom, capable of measuring both acceleration and rotation for x-axis 121, y-axis 122, and z-axis 123. In some examples, a motion sensor with multiple degrees of freedom available may be selectively configured to only activate and/or provide measurements for less than all of its available degrees of freedom, for example to reduce power consumption of motion sensing device 100. In some examples, motion sensing device 100 may be configured to set or modify a sampling rate for the motion sensor, to determine a rate at which motion signals are provided. For example, motion signals providing measurements of motion of motion sensing device 100 may be measured at a rate of 200 Hz. An individual motion sample may be referred to as a "sample", and motion signals for an individual degree of freedom may be referred to as a "channel."

Figure 2:
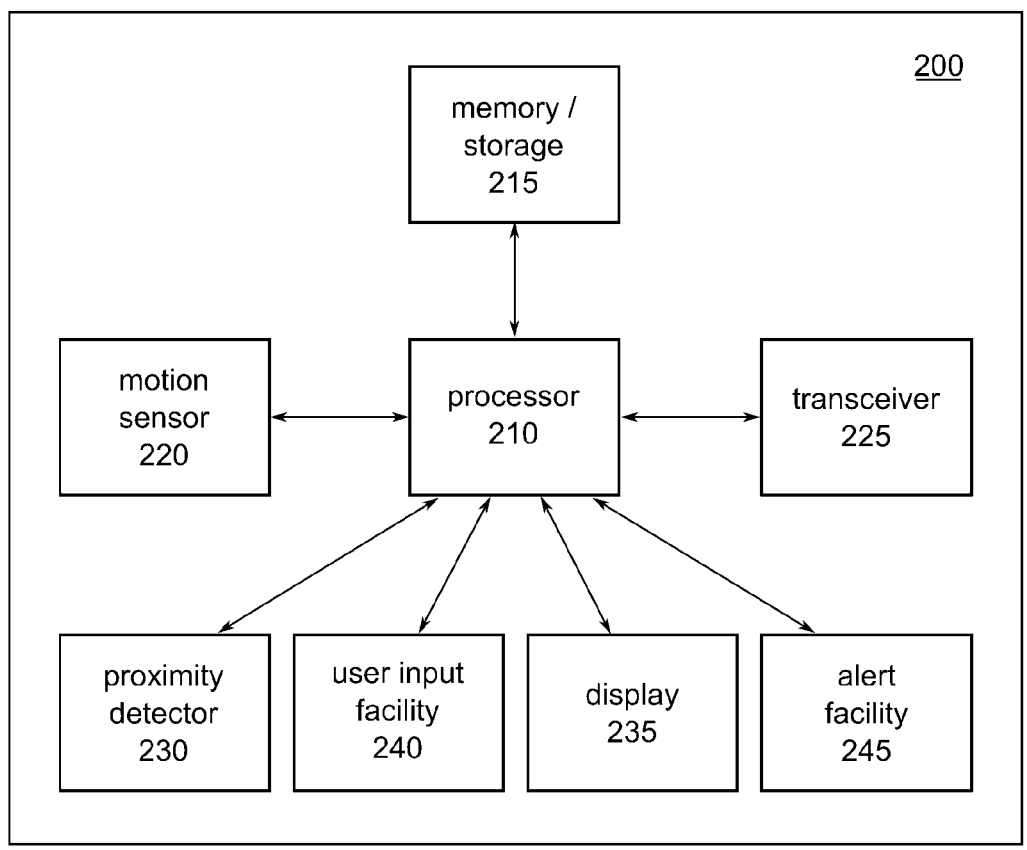
FIG. 2 illustrates an example internal schematic structure of a wearable motion sensing device 200, such as, for example, motion sensing device 100.

FIG. 2 illustrates an example internal schematic structure of a wearable motion sensing device 200, such as, for example, motion sensing device 100. The illustrated components are mounted in a housing (not illustrated in FIG. 2) of motion sensing device 200 and include, among others, processor 210, configured to receive and execute instructions stored in memory/storage 215. In some examples, some of the components illustrated in FIG. 2 may not be included; however, motion sensor 200 is a required component. Processor 210 may also be configured to store and retrieve data to and from memory/storage 215. Motion sensing device 200 includes the memory/storage 215, which is configured to provide instructions and/or data to processor 210, such as via a bus. Memory/storage 215 may include a nontransitory storage medium for storing the instructions. In some examples, more than one processor 210 and/or more than one memory/storage 215 may be included in motion sensing device 200. In some examples, some of the features described may be performed by processor 210 in hardware, rather than being implemented by instructions executed by processor 210.

Motion sensing device 200 includes motion sensor 220, which is configured to provide motion signals to processor 210. Motion sensing device 220 may also be controlled by processor 210, such as, but not limited to, starting and stopping the collection of motion signals, and enabling various power saving features, such as varying a sampling rate or varying a number of active degrees of freedom. The above discussion of the motion sensor included in motion sensing device 100 applies to motion sensor 220.

In some examples, motion sensing device 200 may include transceiver 225, connected to processor 210, for exchanging information with one or more external devices. Transceiver 225 may send and/or receive information wired and/or wirelessly with one or more external devices. For example, transceiver 225 may configured to communicate via one or more well-known techniques, such as, but not limited to, WiFi, Bluetooth, a cellular data network, or USB, according to one or more well-known protocols, such as, but not limited to, TCP/IP. Processor 210 may be configured to use transceiver 225 to communicate with external devices to send and/or receive data. Processor 210 may be configured to use transceiver 225 to issue commands to one or more external computing devices. Processor 210 may be configured to receive commands via transceiver 225, perform processing in response to the received commands, and/or transmit a response to a received command via transceiver 225. Thus, by use of transceiver 225, various aspects described below may be selectively implemented within motion sensing device 200 or one or more external devices that can communicate with motion sensing device 200 via transceiver 225. In some examples, processor 210 may be configured to merely buffer motion signals obtained from motion sensor 220 and periodically and/or on request transmit the motion signals via transceiver 225 for processing by one or more external computing devices, thereby extending the battery life of wearable motion sensing device 200. In some examples, motion sensing device 200 may be essentially self-contained, with processor 210 configured to, without assistance from an external computing device, detect when the user performs certain actions, and determine when medication has been taken by the user.

In some examples, motion sensing device 200 may include a proximity detector 230 connected to processor 210. Proximity detector 230 is configured to generate a proximity signal in response to the user being in proximity to a container containing a medication. In some examples, proximity detector is configured to detect a presence of the container. In some examples, the proximity signal may include, or processor 210 may be configured to determine based on the proximity signal, an identification of a container. In some examples, proximity signal may include, or a processor, such as processor 210, may be configured to determine based on the proximity signal, a unique identifier for a container. In some examples, the proximity signal identifies, or a processor, such as processor 210, may be configured to determine based on the proximity signal, a content of a container. In some examples, proximity detector 230 may include an RFID reader configured to generate a proximity signal indicating that the RFID reader is in proximity to an RFID tag, such as an inexpensive passive RFID tag, attached to a container. In some examples, proximity detector 230 may rely on other proximity detection techniques, such as, but not limited to, near-field identification (NFID) and Bluetooth Low Energy.

In some examples, a proximity detector not included in motion sensing device 200 may be included in a medication adherence monitoring system including motion sensing device 200. In some examples, a companion device on or with the user, such as smartphone 320 illustrated in FIG. 3, may include a proximity detector. In some examples, a proximity detector is configured to detect a presence of the user or motion sensing device 200. For example, a container may include an RFID reader and motion sensing device 200 may include an RFID tag.

Motion sensing device 200 may also include a display 235. For example, where motion sensing device 200 is provided by a "smart watch" such as an Apple Watch or a Pebble SmartWatch, display 235 may include an LCD screen, LED screen, or OLED screen. Display 235 is controlled by processor 210, which may be configured to display text and/or graphical elements on display 235. In some examples, display 235 may include one or more discrete light emitting elements, such as, but not limited to, an LED. In such examples, processor 210 may be configured to turn on, turn off, blink, and/or change color of the one or more discrete light emitting elements. Processor 210 may also be configured to respond to commands received via transceiver 225 so as to present a visual indication to a user via display 235. In some examples, a medication adherence monitoring system including motion sensing device 200 may include a display outside of motion sensing device 200. For example, a companion external computing device on or with a user may include a display, and a medication adherence monitoring system including the companion external computing device and motion sensing device 200 may cause presentation of an indication via the display of the companion external computing device in response to information obtained by motion sensing device 200. In some examples, processor 210 may be configured to visually display an alert on display 235.

Motion sensing device 200 may also include user input facility 240. Processor 210 is configured to obtain user input information via user input facility 240. In some examples in which motion sensing device 200 includes a graphical display 235, user input facility 240 may include a touch sensor integrated with display 235. User input facility 240 may also include a touch sensor independent of a display. User input facility 240 may include a button. Processor 210 may be configured to process motion signals obtained from motion sensor 220 to recognize gestural user input. In some examples, a medication adherence monitoring system including motion sensing device 200 may be configured to present a request for user input, such as a prompt, via display 235, and receive a responsive user input via user input facility 240. In some examples, a medication adherence monitoring system including motion sensing device 200 may include a user input facility outside of motion sensing device 200. For example, a companion external computing device on or with a user may include a user input facility.

Motion sensing device 200 may also include alert facility 245. Processor 210 is configured to control alert facility 245. Alert facility 245 may be configured to cause motion sensing device 200 to vibrate, such as by including a vibration motor. Alternatively of additionally, the alert facility 245 may be configured to generate an audible alert, such as by including a speaker. The processor 210 may be configured to respond to commands received via transceiver 225 so as to present an alert to a user via alert facility 245. In some examples, a medication adherence monitoring system including motion sensing device 200 may include an alert facility outside of motion sensing device 200. For example, a companion external computing device on or with a user may include an alert facility.

Figure 3:
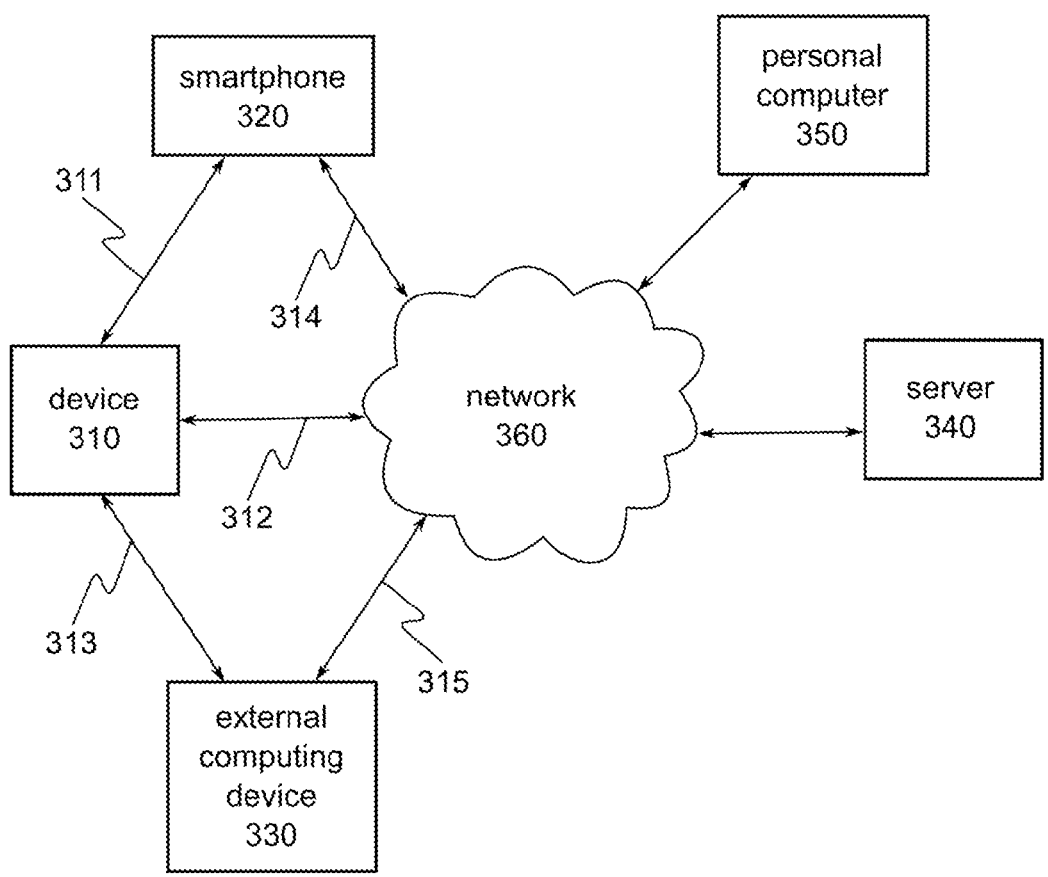
FIG. 3 illustrates an example schematic structure of a medication adherence monitoring system 300.

FIG. 3 illustrates an example schematic structure of a medication adherence monitoring system 300. In some examples, some of the components illustrated in FIG. 3 may not be included; however, motion sensing device 310 worn by a user is a required component. Medication adherence monitoring system 300 includes motion sensing device 310. The above discussion of the motion sensor included in motion sensing device 100 applies to motion sensor 220. In some examples, medication adherence monitoring system 300 may consist only of motion sensing device 310. In some examples, various features of medication adherence monitoring system 300 may be implemented across some or all of motion sensing device 310, smartphone 320, external computing device 330, server 340, and personal computer 350, by use of communication performed via network 360, communication link 311, and/or communication link 313. Other computing devices, although not illustrated in FIG. 3, may also be included in, or interact with, medication adherence monitoring system 300 via network 360. Each of motion sensing device 310, smartphone 320, external computing device 330, server 340, and personal computer 350 includes one or more processors each configured to execute instructions, and one or more nontransitory storage mediums which cause the processors to implement various features of medication adherence monitoring system 300.

Network 360 provides communication facilities allowing the components illustrated in FIG. 3 to interact. In some examples, network 360 may include a cellular data network. In some examples, network 360 may include a local area network, which may include, for example, a wireless access point. In some examples, network 360 may include a wide area network, such as the Internet.

In some examples, a transceiver included in motion sensing device 310, such as transceiver 225, may be configured to communicate directly with network 360 via network communication link 312. In some examples, a transceiver included in motion sensing device 310 may be configured to connect directly to smartphone 320 via local communication link 311. In some examples, a transceiver included in motion sensing device 310 may be configured to connect indirectly to smartphone 320 via network communication links 312 and 314. In some examples, a transceiver included in motion sensing device 310 may be configured to connect directly to external computing device 330 via local communication link 313. In some examples, a transceiver included in motion sensing device 310 may be configured to connect indirectly to external computing device 330 via network communication links 312 and 315.

Medication adherence monitoring system 300 may include smartphone 320. Although item 320 is referred to as a "smartphone," this term is intended as a contemporary reference, as item 320 more broadly described is a portable computing device kept on or with a user wearing motion sensing device 310. Much as mentioned above, smartphone 320 may be configured to act as a companion device for motion sensing device 310. For example, smartphone 320 may be configured to obtain motion signals from motion sensing device 310, and perform all of or most of the rest of the features of medication adherence monitoring system 300. As smartphone 320 generally has more battery life, computational power, and display and input area, it can serve as an effective interface for motion sensing device 310, as well as reduce the power requirements of and size of motion sensing device 310. Additionally, as smartphone 320 is on or with a user wearing smartphone 320, it is readily accessible, and in general may communicate with motion sensing device 310 more frequently than external computing device 330, server 340, and personal computer 350.

Medication adherence monitoring system 300 may include external computing device 330. In general, external computing device 330 may provide similar capabilities as smartphone 320, and is generally in the control of the user of motion sensing device 310, but lacks the degree of portability of smartphone 320. In some examples, external computing device 330 may be a tablet computer, a notebook computer, or a desktop computer. As external computing device 330 is less frequently in proximity to motion sensing device 310, communication via local communication link 313 may be less frequent than via local communication link 311.

Medication adherence monitoring system 300 may also include server 340. In some examples, a single server 340 is included in medication adherence monitoring systems 300 for multiple users. In some examples, server 340 may be configured to provide updates to instructions stored in various nontransitory computer readable storage mediums included in medication adherence monitoring system 300, In some examples, server 340 may be configured to store backups of user-specific template signals, and provide stored backups to other components of medication adherence monitoring system 300. In some examples, server 340 may be configured with a web-based interface to allow the user or healthcare providers to interact with medication adherence monitoring system 300. In some examples, server 340 may interact with medication adherence monitoring system 300, but not necessarily be part of medication adherence monitoring system 300. Although one server 340 is illustrated, there may be multiple servers 340.

Medication adherence monitoring system 300 may also include personal computer 350. Personal computer 350 may be operated by a healthcare provider, and configured to review records of medication adherence recorded by medication adherence monitoring system 300. Personal computer 350 may be configured to specify medication schedules for a user of medication adherence monitoring system 300. In some examples, personal computer 350 may interact with medication adherence monitoring system 300, but not necessarily be part of medication adherence monitoring system 300. Although one personal computer 350 is illustrated, there may be multiple personal computers 350.

In some examples, in which it is desired to monitor medication adherence for a medication in pill form stored in a pill bottle, it may be of particular interest to detect when two actions are performed by the user: a first "twist-cap" action associated with opening a pill bottle container, and a second "hand-to-mouth" action associated with transporting a pill from the pill bottle to the user's mouth. In some cases, particularly in the United States, opening the pill bottle container may require dealing with a child-proof cap. In some examples, there may be other medication containers of interest, such as, but not limited to, foil-wrapped pills, syrup containers, and cream tubes. In some examples, in which it is desired to monitor medication adherence for foil-wrapped pills, it may be of particular interest to detect when two actions are performed by the user: a first "push" action associated with removing a pill from its foil-wrapped container, and a second "hand-to-mouth" action associated with transporting the pill from the container to the user's mouth. In some examples, in which it is desired to monitor medication adherence for medication in a syrup container, it may be of particular interest to detect when two or more actions are performed by the user from among: a first "twist-cap" action associated with opening a syrup container; a second "measuring" action associated with pouring the medication into a cup or spoon, or otherwise obtaining a measured amount from the syrup container (including, but not limited to, use of a syringe); and a third "hand-to-mouth" action associated with transporting the measured amount of syrup to the user's mouth. In some cases, particularly in the United States, opening the syrup container may require dealing with a child-proof cap. In some examples, in which it is desired to monitor medication adherence for medication in a cream tube, it may be of particular interest to detect when two or more actions are performed by the user from among: a first "twist-cap" action associated with opening a cap of the cream tube container; a second "squeeze" action associated with squeezing medication out of the tube onto a user's hand or body; a third "hand-to-body" action associated with moving a hand with cream to the body for application; and a fourth "rub" action associated with applying the cream to the user's body. Additional actions may be identified for the above containers, and additional actions may be identified for other medication containers. In general, it is desirable, although not required, to select actions that are identifiable based on motion signals obtained from motion sensing device 310, and different from ordinary daily activities.

Figure 4:
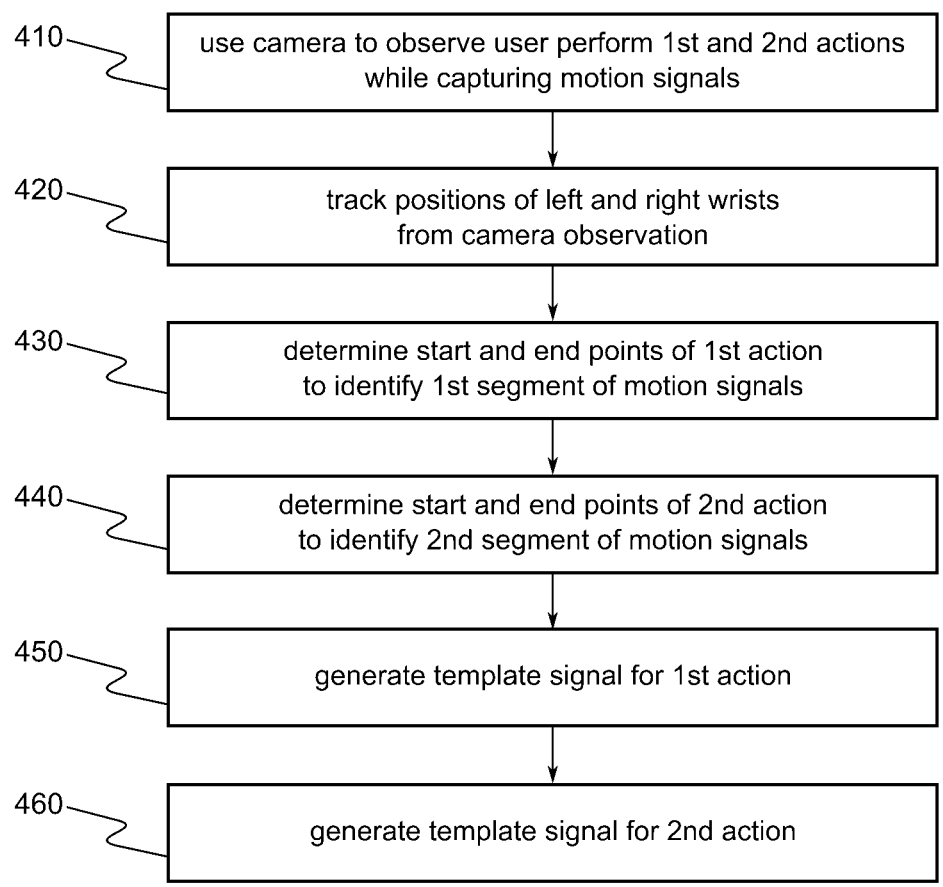
FIG. 4 illustrates aspects of methods for generating template signals for recognizing actions performed by a user, such as an initial set of template signals.

FIG. 4 illustrates aspects of methods for generating template signals for recognizing actions performed by a user, such as an initial set of template signals. In some implementations, these methods, or portions of these methods, may be implemented using a processing device, for example, but not limited to, a computer, a server, or some other suitable device. The processing device may include one or more processing units that execute instructions for operating various components to generate an initial set of template signals for a user. The processing unit may be a microprocessor or microcontroller, a field-programmable gate array (FPGA), a digital signal processor (DSP), or some other suitable unit that is capable of processing instructions and/or data. In some implementations, the instructions and recorded data (such as the captured images) may be stored in memory associated with the processing device. The memory may be one of a hard disk, flash memory, read-only memory (ROM), random access memory (RAM), or some suitable combination of these, or some other memory that is capable of storing instructions and/or data. In some implementations, the instructions may be configured by a user, for example, but not limited to, an operator using a user input interface (for example, a keyboard, touch screen, and/or a mouse coupled to the processing device).

At 410, a user wears motion sensing device 310 and performs first and second actions, such as the actions described in the previous paragraph. While the user performs the first and second actions, motion signals obtained from motion sensing device 310 are captured, and a camera is used to observe the user performing the first and second actions. In some examples, the camera is an RGB-Depth camera, such as the Kinect introduced by Microsoft. In general, it is preferable, but not necessary, that the first and second actions are performed sequentially.

At 420, positions of the left and right wrists are tracked based on the camera observations. In an example utilizing the Kinect and detecting a first "twist-cap" action and a second "hand-to-mouth" action for a pill bottle, Kinect SDK software allows tracking 20 body joints.

At 430, start and end points of the first action are determined to identify a first segment of the captured motion signals that corresponds to the user having performed the first action. At 440, start and end points of the second action are determined to identify a second segment of the captured motion signals that corresponds to the user having performed the first action. In the above example utilizing the Kinect and detecting a first "twist-cap" action and a "hand-to-mouth" action for a pill bottle, in order to identify the portions of relatively long duration motion signals that correspond to the two actions of twist-cap and hand-to-mouth, the user goes through a training phase by sitting/standing in front of the Kinect camera. The Kinect camera is then used to automatically determine the start and end of the motion signals corresponding to the two actions by tracking the joint positions via the SDK software. This software is programmed to detect the twist-cap action by using the positions of the left and right wrists denoted by $P_{lw}(x_{lw}, y_{lw}, z_{lw})$ and $P_{rw}(x_{rw}, y_{rw}, z_{rw})$, the hand-to-mouth action by using the positions of the right wrist (the roles are reversed for left-handed users), and the shoulder center denoted by $P_{sc}(x_{sc}, y_{sc}, z_{sc})$. More specifically, the pose detection, which is a built-in function of the Kinect SDK, is used to trigger the detection of the twist-cap or hand-to-mouth actions. In other words, the user is asked to start with his/her own pose $\Psi$ before performing a twist-cap or hand-to-mouth action. The start and end of a twist-cap action is then determined sequentially by measuring the closeness between the two wrists via $|x_{lw}-x_{rw}|$. The procedure is provided as a pseudo-code in Algorithm 1 of U.S. Provisional Patent Application Ser. No. 62/040,531, filed on Aug. 22, 2014, which was incorporated by reference above.

At the same time, the inertial sensor signals between the time stamps $t_s$ and $t_e$ are obtained to form a template of a user-specific twist-cap action. The detection of the hand-to-mouth action is achieved similarly. The start is determined by $0 < y_{hc} - y_{rw} \leq \mu$ and the end is determined by $y_{hc} - y_{rw} > \mu$, where $\mu=15$ cm was experimentally found to work well across different users. This training phase allows creating inertial signal templates for the two actions of "twist-cap" and "hand-to-mouth". Basically, the Kinect camera is used during a training phase in order to obtain the inertial sensor signal segments which correspond to the two actions of interest by automatically time stamping the start and end of the actions.

Figure 5A:
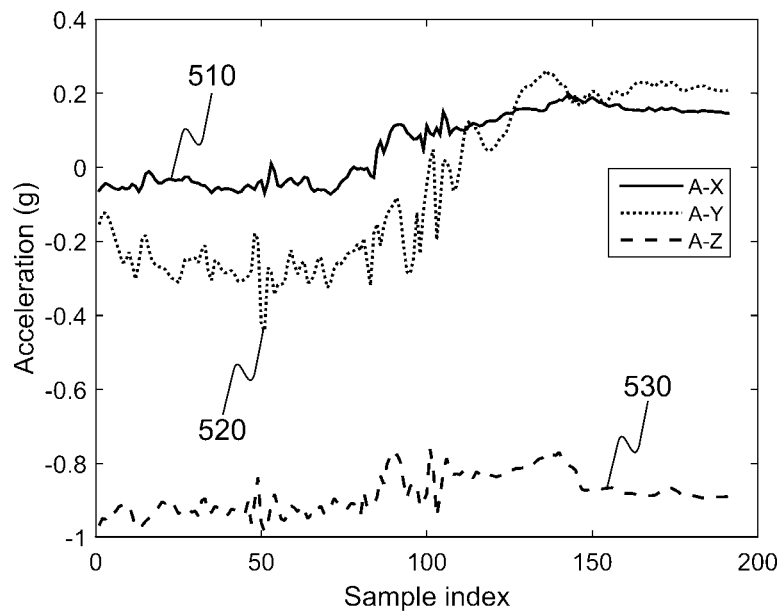
FIG. 5A illustrates example plots of user-specific template signals generated for a first "twist-cap" action associated with opening a pill bottle.
Figure 5B:
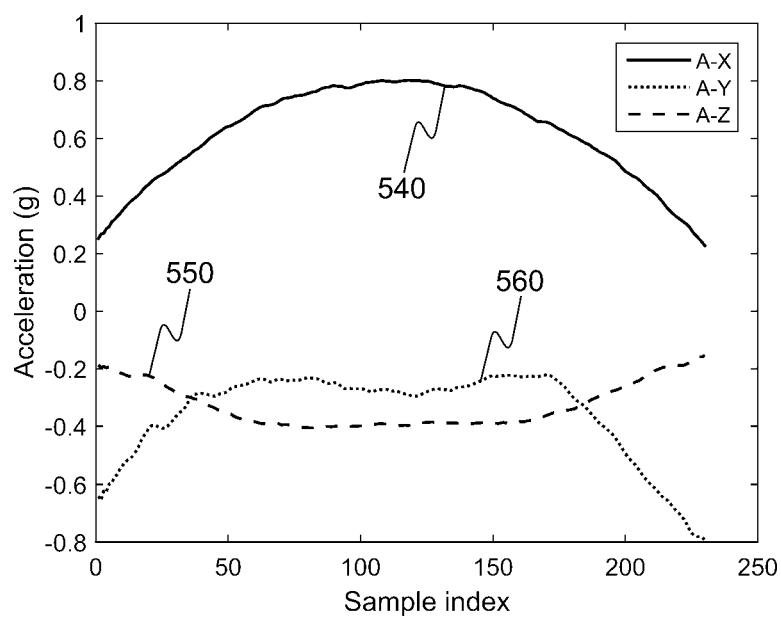
FIG. 5B illustrates example plots of user-specific template signals generated for a second "hand-to-mouth" action associated with transporting a pill from a pill bottle to the user's mouth.

At 450, a first template signal is generated for the first action based on the identified first segment of the motion signals. At 460, a second template signal is generated for the second action based on the identified second segment of the motion signals. In some examples, a training phase, such as the example discussed above with respect to 430 and 440 of FIG. 4, may include the user performing the first and second actions multiple times, such as five times, resulting in multiple signal segments identified for the first and second actions. Templates of the two actions are then generated by taking averages of the signal segments after resampling the signal segments to have the same normalized length before averaging. FIG. 5A illustrates example plots of user-specific template signals generated for a first "twist-cap" action associated with opening a pill bottle. Plot 510 illustrates a template signal to be matched against motion signals for acceleration in the x-axis direction, plot 520 illustrates a template signal to be matched against motion signals for acceleration in the y-axis direction, and plot 530 illustrates a template signal to be matched against motion signals for acceleration in the z-axis direction. FIG. 5B illustrates example plots of user-specific template signals generated for a second "hand-to-mouth" action associated with transporting a pill from a pill bottle to the user's mouth. Plot 550 illustrates a template signal to be matched against motion signals for acceleration in the x-axis direction, plot 560 illustrates a template signal to be matched against motion signals for acceleration in the y-axis direction, and plot 570 illustrates a template signal to be matched against motion signals for acceleration in the z-axis direction.

Figure 6:
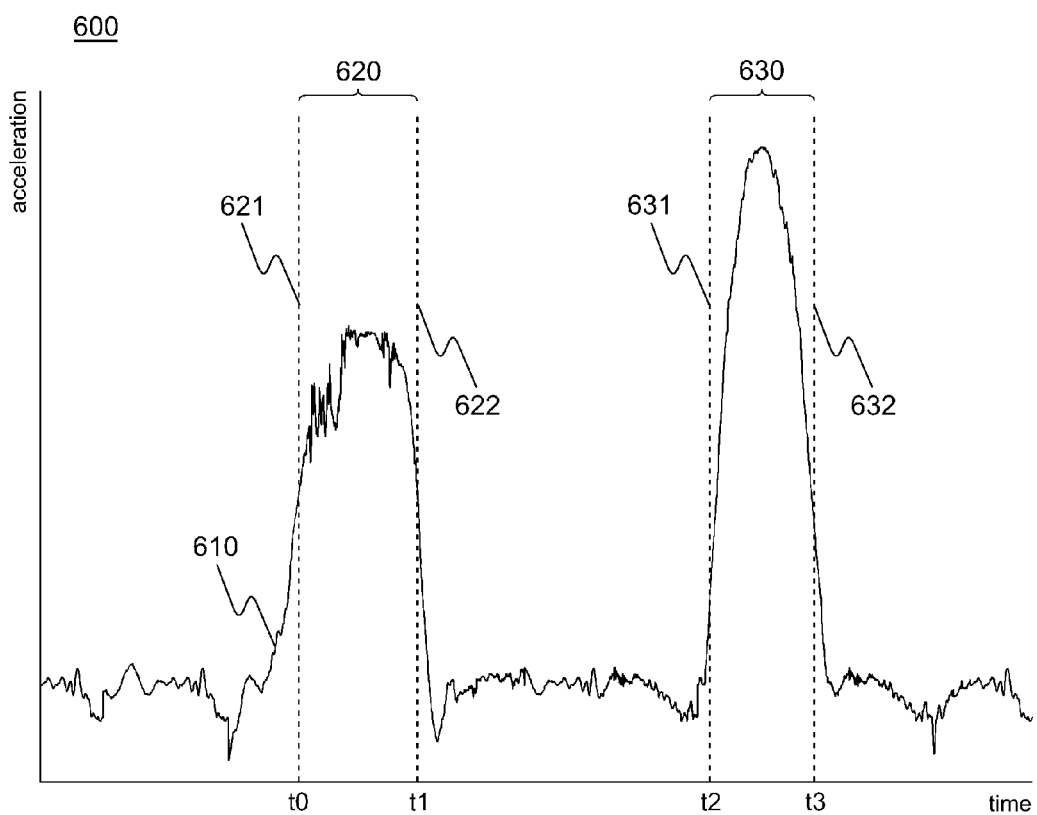
FIG. 6 illustrates a plot 600 of motion signals 610 sensed by a motion sensor worn on a user's wrist or forearm, and examples of identifying motion signal segments 620 and 630 of the motion signals corresponding to the user performing first and second actions for taking a medication.

FIG. 6 illustrates a plot 600 of motion signals 610 sensed by a motion sensor worn on a user's wrist or forearm, and examples of identifying motion signal segments 620 and 630 of the motion signals corresponding to the user performing first and second actions for taking a medication. Plot 600 illustrates motion signals 610 obtained while the user performs the first and second actions while wearing the motion sensor included in wearable motion sensing device 310. Although plot 600 shows x-axis acceleration motion signals 610 and identifying motion signal segments 620 and 630 for a first "twist-cap" action associated with opening a pill bottle and a second "hand-to-mouth" action associated with transporting a pill from a pill bottle to the user's mouth, the discussion of FIG. 6 is more generally applicable to other sources of motion signals and different first and second actions.

Since the first action and the second action take place sequentially for taking the medication, medication adherence monitoring system 300 first tries to detect the first action based on the obtained motion signals 610. A first template signal corresponding to the first action, such as the template signal illustrated by plot 510 in FIG. 5A, is used to identify a first motion signal segment 620 of motion signals 610. In some examples, a sliding or moving window may be used to attempt to match the first template signal against motion signals 610 by utilizing the dynamic time warping (DTW) technique. DTW is known to be an effective matching algorithm for measuring similarity between two time series which may have different lengths or durations, as discussed in D. Berndt and J. Clifford, "Using dynamic time warping to find patterns in time series," KDD Workshop, Seattle, Wash., vol. 10, no. 16, pp. 359-370, 1994; and E. Keogh and M. Pazzani, "Derivative dynamic time warping," Proceedings of SIAM International Conference on Data Mining, Chicago, Ill., 2001, both of which are incorporated by reference in their entireties. The window size may be chosen to be the average length of the segmented signals during the training phase. Let w indicate the window size. For example, the sliding window can be shifted by w/4 with the overlap of 3w/4 between neighboring windows. In some examples, the first template signal is matched against the obtained motion signals 610 in real time or near real time. In some examples, medication adherence monitoring system 300 may be configured to buffer the obtained motion signals, and perform less frequent analysis of the obtained motion signals for monitoring medication adherence; for example, motion sensing device 310 may be configured to store an entire day's motion signals, and transmit the entire day's motion signals to external computing device 330 or server 340. In some examples, motion sensing device 310 may be configured to store motion signals during periods that it is unable to transmit the motion signals for analysis, and then transmit the stored motion signals once transmission becomes possible. In some examples, more than one template signal may be associated with an action and matched against obtained motion signals, to reflect variations in how a given user performs an action.

Figure 7A:
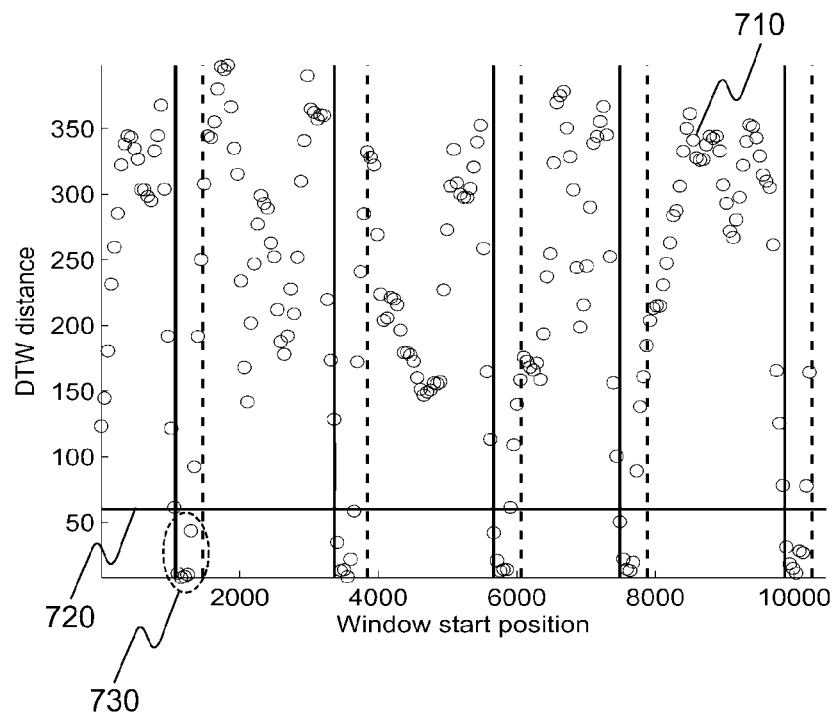
FIGS. 7A and 7B illustrate an example of matching a first template signal against motion signals using a sliding window technique to detect when a user performs a first action.
Figure 7B:
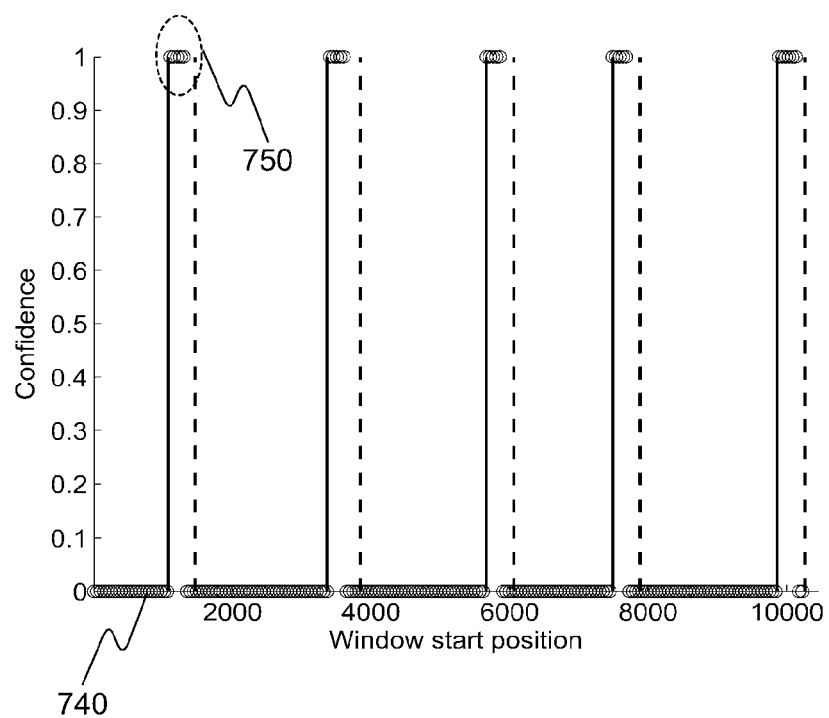

FIGS. 7A and 7B illustrate an example of matching a first template signal against motion signals using a sliding window technique to detect when a user performs a first action, much as discussed above. In FIGS. 7A and 7B, solid and dashed lines indicate the start and end of the first action, respectively, which were found by visual inspection of video recorded while obtaining the motion signals underlying FIGS. 7A and 7B. Use of DTW is illustrated in FIG. 7A, but there are many other well-known techniques effective for measuring similarity between the first template signal and the motion signals. In FIG. 7A, the underlying motion signal is not the same as motion signal 610 in FIG. 6. In FIG. 7A, the circles, such as circle 710, show DTW distances calculated between the first template signal and the motion signals within each sliding window. Detection threshold 720 is used to detect when the DTW distance indicates the action took place. For example, the DTW distances shown in area 730 each are below the detection threshold 720. In some examples, system 300 may use an increased detection threshold 720 during a period of a user's initial use of system 300, and may reduce detection threshold 720 over time. In some examples, detection threshold 720 may be dynamically adjusted in response to certain events, such as obtaining a proximity signal indicating that the user is in proximity to a container of medication.

In FIG. 7B, DTW distances smaller than detection threshold were assigned a confidence value of 1, and 0 otherwise, the confidence value indicating a confidence in whether the first motion signal segment matches a sliding window of the motion signals. In some examples, detection robustness may be increased by considering a majority vote over a number of consecutive 1's. In some examples, the confidence value may take intermediate values between 0 and 1 based on the DTW distance, in some examples also based on a relationship to a threshold distance value. In some examples, medication adherence monitoring system 300 may be configured to, in response to the confidence level not clearly indicating a match, cause a presentation of a request to a user for confirmation that a action was actually performed or a medication actually taken, and base a determination as to whether the medication was taken based on a response to the request (such as determining the medication was taken due to a positive response). In such examples, medication adherence monitoring system 300 may also be configured to, in response to the response being positive, revise the first template signal or generating a new template signal for the first action based on a motion signal segment corresponding to the confidence level not having clearly indicating a match.

Returning to FIG. 6, the drawing indicates that medication adherence monitoring system 300 detected the user performed the first action based on first motion signal segment 620, such as, for example, first motion signal segment 620 matching the first template signal much as discussed above. First motion signal segment 620 consists of the motion signals 610 beginning at time 621 (t0) and ending at time 622 (t1).

After detecting that the user performed the first action based on the first motion segment 620, medication adherence monitoring system 300 then tries to detect the second action based on the obtained motion signals 610. A second template signal corresponding to the second action, such as the template signal illustrated by plot 550 in FIG. 5B, is used to identify a first motion signal segment 620 of motion signals 610. The same techniques described above in connection with obtaining first motion signal segment 620 and detecting that the first action was performed based on first motion signal segment 620, can likewise be used for detecting the user performing the second action. FIG. 6 indicates that medication adherence monitoring system 300 detected the user performed the second action based on second motion signal segment 630, such as, for example, second motion signal segment 630 matching the second template signal much as discussed above. Second motion signal segment 630 consists of the motion signals 610 beginning at time 631 (t2) and ending at time 632 (t3).

Although FIG. 6 illustrates matching of a template signal against motion signals from a single channel of motion signals information, both the motion signals and the template signals may be for multiple channels. For example, if motion sensing device includes a six DOF inertial sensor (for example, 3 axes of acceleration and 3 axes or rotation), a six channel (or less than six channel) template signal may matched against the multi-channel motion signals. In such examples, a multi-dimensional matching algorithm may be employed. In some examples, the motion signals may be obtained via multiple motion sensors. In some examples, motion signals may be obtained via multiple motion sensing devices 310 worn by a single user; for example, a user may wear a motion sensing device 310 on each wrist to enhance recognition accuracy.

Figure 8:
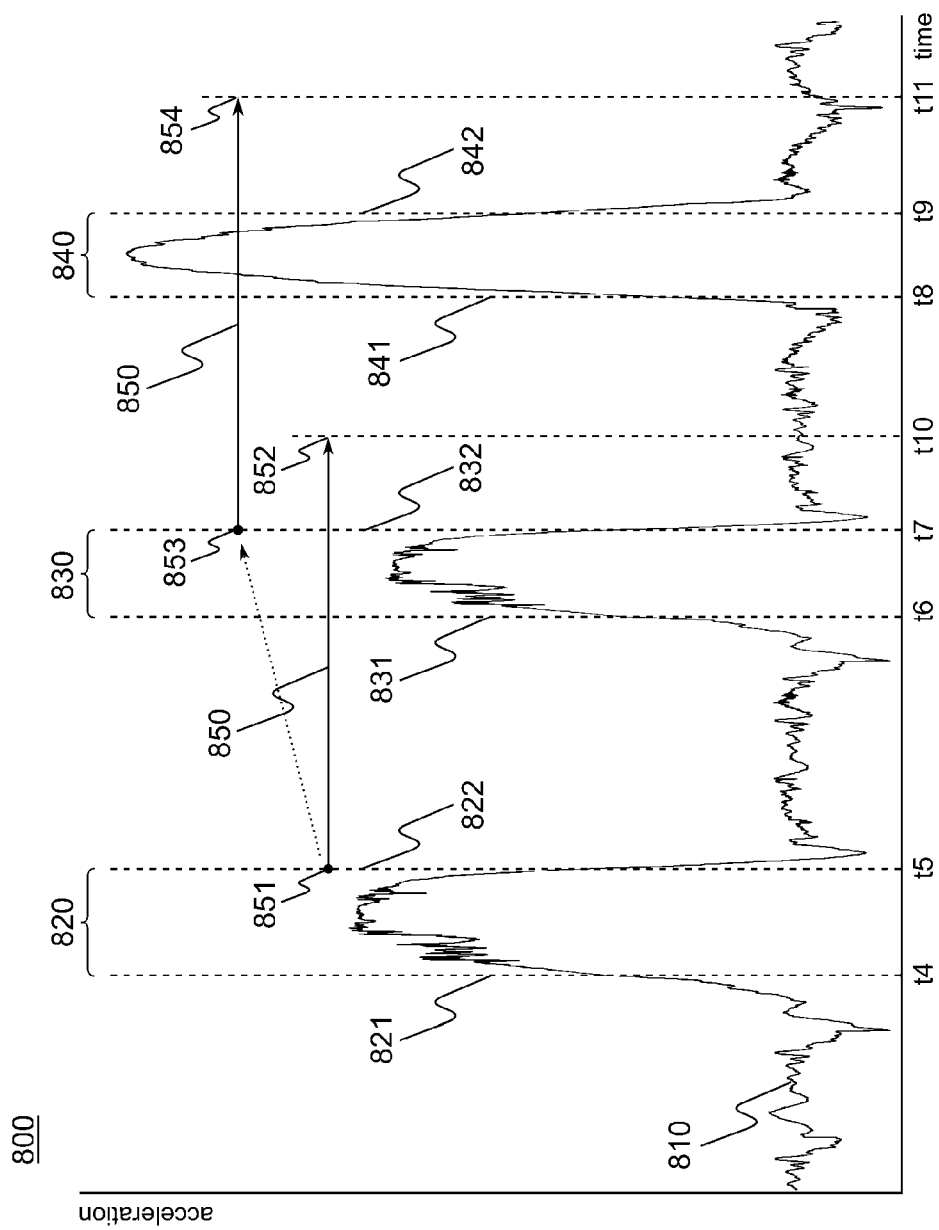
FIG. 8 illustrates a plot 800 of motion signals sensed by a motion sensor worn on a user's wrist or forearm, and examples of identifying motion signal segments 820, 830, and 840 and use of a time period 850 for determining when a medication has been taken.

FIG. 8 illustrates a plot 800 of motion signals sensed by a motion sensor worn on a user's wrist or forearm, and examples of identifying motion signal segments 820, 830, and 840 and use of a time period 850 for determining when a medication has been taken. Plot 800 illustrates motion signals 810 obtained while the user performs the first and second actions while wearing the motion sensor included in wearable motion sensing device 310. Although plot 800 illustrates x-axis acceleration motion signals 810 and identifying motion signal segments 820, 830, and 840 for a first "twist-cap" action associated with opening a pill bottle and a second "hand-to-mouth" action associated with transporting a pill from a pill bottle to the user's mouth, the discussion of FIG. 8 is more generally applicable to other sources of motion signals and different first and second actions.

Much as discussed above with respect to FIG. 6, medication adherence monitoring system 300 first tries to detect the first action based on the obtained motion signals 810. FIG. 8 indicates that medication adherence monitoring system 300 detected the user performed the first action based on first motion signal segment 820, which consists of the motion signals 810 beginning at time 821 (t4) and ending at time 822 (t5). In response to the detection of the first action based on first motion signal segment 820, a time period 850 may be initiated to begin at a time associated with first motion signal segment 820. In the particular example illustrated in FIG. 8, start 851 of time period 850 is at ending time 822 (t5) of first motion signal segment 820. Time period 850 has a time duration, which may be user-specified or user-specific, extending to end 852 (at time t10). If the second action is not detected within the time duration (in other words, by time t10), medication adherence monitoring system 300 returns to trying to detect the first action.

While trying to detect the second action after time 822 (t5) within time period 850, medication adherence monitoring system 300 may also trying to detect whether the first action is performed. In the specific example illustrated in FIG. 8, medication adherence monitoring system 300 detected the user performed the first action based on second motion signal segment 830, which consists of the motion signals 810 beginning at time 831 (t6) and ending at time 832 (t7). In response to the detection of the first action based on first motion signal segment 830, the time period 850 may be reinitiated to begin at a time associated with second motion signal segment 830. In the particular example illustrated in FIG. 8, time period 850 is reinitiated to start at start 853, which is at ending time 832 (t7) of second motion signal segment 830. Time period 850 maintains the same time duration, and now extends to end 853 (at time t11).). If the second action is not detected within the reinitiated time duration (in other words, by time t11), medication adherence monitoring system 300 returns to trying to detect the first action. However, in the specific example illustrated in FIG. 8, medication adherence monitoring system 300 detected the user performed the second action based on third motion signal segment 840 before end time 854 (t11), with third motion signal segment 840 consisting of the motion signals 810 beginning at time 841 (t8) and ending at time 842 (t9).

Figure 9:
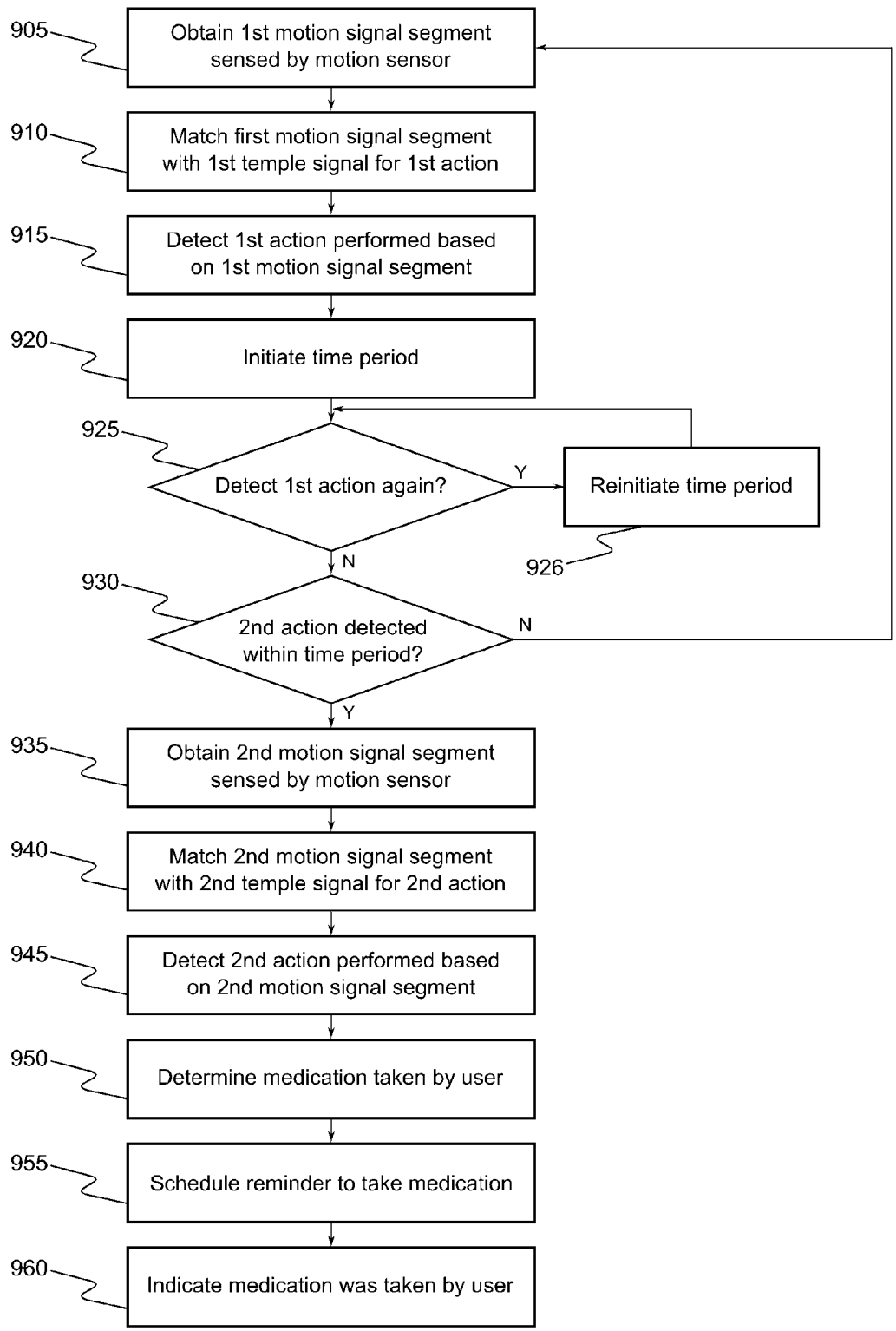
FIG. 9 illustrates examples of methods for monitoring medication adherence.

FIG. 9 illustrates examples of methods for monitoring medication adherence. The above discussion of FIGS. 1-8 is relevant to these methods. In some implementations, these methods, or portions of these methods, may be implemented using a processing device, for example, but not limited to, a computer, a server, or some other suitable device. The processing device may include one or more processing units that execute instructions for operating the various components of the system 300 to monitor medication adherence. The processing unit may be a microprocessor or microcontroller, a field-programmable gate array (FPGA), a digital signal processor (DSP), or some other suitable unit that is capable of processing instructions and/or data. In some implementations, the instructions and recorded data (such as the captured images) may be stored in memory associated with the processing device. The memory may be one of a hard disk, flash memory, read-only memory (ROM), random access memory (RAM), or some suitable combination of these, or some other memory that is capable of storing instructions and/or data. In some implementations, the instructions may be configured by a user, for example, but not limited to, an operator of the system 300 using a user input interface (for example, a keyboard, touch screen, and/or a mouse coupled to the processing device).

At 905, medication adherence monitoring system 300 obtains a first motion signal segment sensed by a motion sensor, included in motion sensing device 310, worn on a user's wrist or forearm. As an illustrative example, FIG. 6 illustrates first motion signal segment 620 included in obtained motion signals 610. At 910, medication adherence monitoring system 300 may be configured to match the first motion signal segment with a first template signal for a first action. This may serve to identify a start and end of the first motion signal segment included in a larger segment of motion signals. The above discussion of FIGS. 6, 7A, and 7B describes illustrative examples of matching a first template with sliding windows to identify a matching first motion signal segment.

At 915, medication adherence monitoring system 300 detects the user performed the first action based on the first motion signal segment. The above discussion of FIGS. 6, 7A, and 7B describes illustrative examples where a match of a template with a sliding window may both identify a first motion signal segment and detect the user performed the first action. At 920, in some examples, medication adherence monitoring system 300 may initiate a time period to begin at a time associated with the sensing of the first motion signal segment. The above discussion of FIG. 8 describes illustrative examples in which a time period 850 is initialized to begin at end time 822 (t5) of first motion signal segment 820. After 920, medication adherence monitoring system 300 may be configured to detect, based on obtained motional signals sensed after the first motion signal segment, both the user performing the first action and the user performing a second action. At 925, in some examples, in response to medication adherence monitoring system 300 detecting the user performed the first action again during the time period, at 926 the time period may be reinitiated to begin at a time associated with the sensing of a motion signal segment corresponding to the user having performed the first action again. The above discussion of FIG. 8 describes illustrative examples in which a first action is detected based on motion signal segment 830, and in response, time period 850 is reinitiated to begin at end time 832 (t7) of motion signal segment 830. At 930, in some examples, in response to the second action not being detected within a predetermined amount of time after the beginning of the time period, such as, for example, by end time 854 (t11) of time period 850 illustrated in FIG. 8, medication adherence monitoring system 300 returns to 905 to try to detect the first action.

At 935, medication adherence monitoring system 300 obtains a second motion signal segment sensed by the motion sensor worn on the user's wrist or forearm. As an illustrative example, FIG. 6 illustrates second motion signal segment 630 included in obtained motion signals 610. At 940, medication adherence monitoring system 300 may be configured to match the second motion signal segment with a second template signal for the second action. This may serve to identify a start and end of the second motion signal segment included in a larger segment of motion signals. The above discussion of FIG. 6 describes illustrative examples of matching a second template with sliding windows to identify a matching second motion signal segment, and the above discussion of FIGS. 7A and 7B describes illustrative examples of matching a template with sliding windows to identify a matching motion signal segment.

At 945, medication adherence monitoring system 300 detects the user performed the second action based on the second motion signal segment. The above discussion of FIG. 6 describes illustrative examples where a match of a second template with a sliding window may both identify a second motion signal segment and detect the user performed the second action, and the above discussion of FIGS. 7A and 7B describes illustrative examples where a match of a template with a sliding window may both identify a motion signal segment and detect the user performed an action.

At 950, medication adherence monitoring system 300 determines the medication was taken by the user based on the detection of the second action. In some examples, a record of the medication having been taken, along with a time and date, may be stored by medication adherence monitoring system 300. In some examples, medication adherence monitoring system 300 may be configured to obtain a confirmation that the medication was taken, to screen false positives. In some examples, the determination that the medication was taken may be based on a confidence level associated with the detection of the first action in 915 and/or a confidence level associated with the detection of the second action in 945; for example, a lower confidence level may be required in response to a proximity signal indication the user is in proximity to a container containing the medication, or a lower confidence level may be required for a predetermined time after alerting a user.

At 955, in some examples, medication adherence monitoring system 300 may be configured to schedule a reminder for the user to take the medication. In some examples, medication adherence monitoring system 300 may have information regarding a schedule on which the user is intended to take the medication, and set a reminder based on the schedule. For example, for a medication that should be taken every 4 hours, if the medication is taken at 9:15 AM, a reminder to take the medication may be scheduled for 1:15 PM. In some examples, the scheduling of a reminder may take into account items on an electronic calendar of the user. In some examples, the scheduling of the reminder may take into account patterns of user behavior, such as typical periods of sleep. In some examples, the reminder may be time-based, such as the above reminder at 1:15 PM. In some examples, the reminder may be event-based; for example, the reminder might indicate to take the medication after the user wakes up in the morning, or on a nurse's next visit with a patient. In some examples, the reminder may be location-based; for example, the reminder might indicate to take the medication the next time the user returns home. In some examples, the reminder may result in medication adherence monitoring system 300 alerting the user directly. In some examples, a reminder may be sent to or created for someone other than the user; for example, a reminder may be automatically scheduled for a nurse in response to medication adherence monitoring system 300 determining that the medication was taken by the user. In some examples, more than one reminder may be scheduled. In some examples, a sensitivity for template signal matching, such as threshold 720 illustrated in FIG. 7A, may be adjusted in relation to temporal proximity reminder to a scheduled reminder; for example, sensitivity may be increased for a predetermined period of time before and/or after a scheduled reminder.

In some examples, medication adherence monitoring system 300 may be configured to identify when a scheduled taking of the medication has been delayed or missed, and in response determine a catch-up schedule and schedule one or more reminders accordingly. For example, if a user is supposed to take a medication four times a day, and on a given day the user was originally scheduled to take the medication at 8:00 AM, 12:00 noon, 4:00 PM, and 8:00 PM, but the 8:00 AM taking is delayed until 11:00 PM, a catch-up schedule of 2:00 PM, 5:00 PM, 8:00 PM might be established, and associated reminders scheduled. In some examples, a health service provider may be contacted in the event of a delayed or missed taking of the medication, and in some such examples, the catch-up schedule may be provided by the health service provider. In some examples, system 300 may adjust a medication schedule in response to detecting that a medication was taken early.

At 960, in response to the determination that the medication was taken by the user, medication adherence monitoring system 300 causes presentation of an indication to the user or transmitting an indication to an external device that the medication was taken by the user. In some examples, a visual, auditory, tactic, and/or haptic indication may be provided to the user concurrent with the determination that the medication was taken by the user, such as, but not limited to, via motion sensing device 310 or smartphone 320. In some examples, medication adherence monitoring system 300 may be configured to record that the medication was taken by the user, along with a record of the time at which the medication was taken, for display of such information to the user that the medication had been taken. In some examples, a medication adherence monitoring system consisting of motion sensing device 310; motion sensing device 310 and smartphone 320; motion sensing device 310 and external computing device 330; or motion sensing device 310, smartphone 320, external computing device 330 may be configured to transmit an indication that the user took the medication to a server on the Internet.

In some examples, medication adherence monitoring system 300 may utilize pre-stored and pre-programmed initial template signals, with the template signals revised and enhanced over time by interactive adaptive training. In some examples, a user may utilize a camera-assisted training protocol to generate and store initial template signals, such as by using the techniques described above in association with FIG. 4, with the template signals revised and enhanced over time by interactive adaptive training.

In some examples, medication adherence monitoring system 300 may be configured to create, modify, and/or replace user-specific template signals used to detect actions performed by the user by use of interactive adaptive training. As a user begins operating system 300, the user can verify if system 300 is operating to the user's expectations. It is desired that system 300 identify medication intake only when the user actually takes the medication, and that system 300 does not generate "false positive" determinations of medication intake when the user does not actually take the medication. System 300 may be configured to receive and process input from the user providing feedback and verifying if system 300 is correctly determining when the user has taken the medication. For example, if the user actually takes the medication, but system 300 fails to determine that the user took the medication, the user may provide a direct indication to system 300, such as, but not limited to, via a user interface on motion sensing device 310 or smartphone 320, that system 300 failed to determine that the user took the medication. In response to a user's input indicating system 300 failed to correctly identify when the user took or did not take a medication, system 300 can review recorded motion signals associated with the incorrect determination, perform template signal matching with greater or less sensitivity, and/or identify a template signal corresponding to the incorrect determination and revise the identified template signal. For example, if system 300 determines that the user took a medication, but the user did not actually take the medication, the user may communicate with system 300 manually, prompting system 300 to review recorded motion signals and adjust matching sensitivity for one or more template signals to avoid similar false positives in the future. The user's manual communication with the system may involve using a menu system or simply following a specific protocol (e.g., tapping on motion sensing device 310 two, three or k number of times). In some examples, motion signal segments from previous determinations may be stored by system 300 for later use for determining an effective sensitivity, modifying template signals, replacing template signals, and/or generating additional template signals.

Although examples are discussed above involving detecting a sequence of two actions, in some examples, detecting a specific sequence of three or more actions may be utilized to determine when a medication has been taken by a user.

In some examples, system 300 may be configured to respond to a proximity signal indicating that a user is in proximity to a medication container. For example, although other techniques for proximity signal generation are known, an RFID tag may be attached to a container containing a medication, and motion sensing device 310 or smartphone 320 may include an RFID reader. In some examples, a proximity signal contemporaneous to detecting the first or second action, such as within a predetermined period of time, may be required for a positive determination that the user took a medication. In some examples, a sensitivity for template signal matching, such as threshold 720 illustrated in FIG. 7A, may be adjusted in response to a proximity signal; for example, sensitivity may be increased for a predetermined period of time after obtaining a proximity signal, as presumably the user is near the container of interest. In some examples, system 300 may be configured to monitor the user's taking of multiple medications, and may use the proximity signal to identify which medication or medications the user has taken.

In some examples, system 300 may be configured to alert a user with an audible or visual signal to take a medication. In some examples, the alert may be generated in response to a reminder, as discussed above. In some examples, a sensitivity for template signal matching, such as threshold 720 illustrated in FIG. 7A, may be adjusted in response to an alert having been generated; for example, sensitivity may be increased for a predetermined period of time after an alert was generated, as presumably the user will take the medication in response to the alert. In some examples, a sensitivity for template signal matching, such as threshold 720 illustrated in FIG. 7A, may be adjusted in response to receiving user input acknowledging an alert; for example, sensitivity may be increased for a predetermined period of time after receiving the user input, as presumably the user will take the medication in response to the alert. In some examples, determination that a medication was taken by the user is based on the first motion signal segment or the second motion signal segment having been sensed within a predetermined period of time after the user has been alerted, as this may be effective in reducing false positive detections.

In some examples, system 300 may be configured to alert a user if it determines the user has taken a medication early. In some examples, system 300 may be configured to alert a user if it determines the user has taken a medication late. In some examples, system 300 may be configured to alert a user if it determines the user has missed a scheduled taking of a medication.

The disclosed and other examples, and portions thereof, may be implemented as one or more computer program products, i.e., one or more modules of computer program instructions encoded on a computer readable medium for execution by, or to control the operation of, data processing apparatus. The implementations can include single or distributed processing of algorithms. The computer readable medium can be a machine-readable storage device, a machine-readable storage substrate, a memory device, or a combination of one or more them. The term "data processing apparatus" encompasses all apparatus, devices, and machines for processing data, including by way of example a programmable processor, a computer, or multiple processors or computers. The apparatus can include, in addition to hardware, code executed by the that creates an execution environment for the computer program in question, for example, but not limited to, code that constitutes processor firmware, a protocol stack, a database management system, an operating system, or a combination of one or more of them.

A system may encompass all apparatus, devices, and machines for processing data, including by way of example a programmable processor, a computer, or multiple processors or computers. A system can include, in addition to hardware, code executed by the hardware that creates an execution environment for the computer program in question, for example, but not limited to, code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (for example, but not limited to, one or more scripts stored in a markup language document), in a single file dedicated to the program in question, or in multiple coordinated files (for example, but not limited to, files that store one or more modules, sub programs, or portions of code). A computer program can be deployed for execution on one computer or on multiple computers that are located at one site or distributed across multiple sites and interconnected by a communications network.

The processes and logic flows described in this document can be performed by one or more programmable processors executing one or more computer programs to perform functions by operating on input data and generating output. The processes and logic flows can also be performed by, and apparatus can also be implemented as, special purpose logic circuitry, for example, but not limited to, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory, or a random access memory, or both. The essential elements of a computer can include a processor for performing instructions and one or more memory devices for storing instructions and data. Generally, a computer can also include, or be operatively coupled to receive data from or transfer data to, or both, one or more mass storage devices for storing data, for example, magnetic, magneto optical disks, or optical disks. However, a computer need not have such devices. Computer readable media suitable for storing computer program instructions and data can include all forms of nonvolatile memory, media and memory devices, including by way of example semiconductor memory devices, for example, but not limited to, EPROM, EEPROM, and flash memory devices; magnetic disks, such as internal hard disks or removable disks; magneto optical disks; and CD ROM and DVD-ROM disks. The processor and the memory can be supplemented by, or incorporated in, special purpose logic circuitry.

While this document may describe many specifics, these should not be construed as limitations on the scope of an invention that is claimed or of what may be claimed, but rather as descriptions of features specific to particular embodiments. Certain features that are described in this document in the context of separate implementations can also be implemented in combination in a single embodiment. Conversely, various features that are described in the context of a single implementations can also be implemented in multiple implementations separately or in any suitable sub-combination. Moreover, although features may be described above as acting in certain combinations and even initially claimed as such, one or more features from a claimed combination in some cases can be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

Only a few examples and implementations are disclosed. Variations, modifications, and enhancements to the described examples and implementations and other implementations can be made based on what is disclosed.

We claim:

1. A method comprising:
    obtaining a first motion signal segment sensed by a motion sensor worn on a user's wrist or forearm;
    detecting the user performed a first action based on the first motion signal segment;
    obtaining a second motion signal segment sensed by the motion sensor, wherein the second motion signal segment was sensed by the motion sensor after the first motion signal segment;
    detecting the user performed a second action based on the second motion signal segment and in response to the detection of the first action;
    determining that a first medication was taken by the user based on the detection of the second action; and
    in response to the determination that the first medication was taken by the user, causing presentation of an indication to the user or transmitting an indication to an external device that the first medication was taken by the user.

2. The method of claim 1, further comprising:
    in response to the detection of the first action based on the first motion signal segment, initiating a time period to begin at a time associated with the sensing of the first motion signal segment,
    wherein the determination that the first medication was taken by the user is further based on a time associated with the sensing of the second motion signal segment having occurred within a predetermined amount of time after the beginning of the time period.

3. The method of claim 2, further comprising:
    obtaining a third motion signal segment sensed by the motion sensor, wherein the third motion signal segment was sensed by the motion sensor after the first motion signal segment;
    detecting the user performed the first action based on the third motion signal segment; and
    in response to the detection of the first action based on the third motion signal segment, reinitiating the time period to begin at a time associated with the sensing of the third motion signal segment.

4. The method of claim 1, wherein the first and second motion signal segments indicate acceleration of the motion sensor along an axis substantially parallel to a longitudinal direction of the user's forearm.

5. The method of claim 1, further comprising:
    identifying a first segment of motion signals sensed by the motion sensor as the first motion signal segment in response to the first segment of motion signals matching a first user-specific template signal generated based on a third motion signal segment sensed by the motion sensor while the user performed the first action at a first time; and
    identifying a second segment of motion signals sensed by the motion sensor as the second motion signal segment in response to the second segment of motion signals matching a second user-specific template signal generated based a fourth motion signal segment sensed by the motion sensor while the user performed the second action at a second time.

6. The method of claim 5, further comprising:
    obtaining a fifth motion signal segment sensed by the motion sensor, wherein the fifth motion signal segment was sensed by the motion sensor after the second motion signal segment;
    detecting the user performed the first action based on the fifth motion signal segment; and
    revising or replacing the first template signal or adding a new template signal based on the first motion signal segment and the fifth motion signal segment.

7. The method claim 5, further comprising:
    calculating a confidence level that the first motion signal segment matches the first template signal;
    in response to the detection of the second action and the confidence level, causing presentation of a request for confirmation that the first medication was taken;
    obtaining a first response to the request indicating that the first medication was taken; and
    in response to the first response indicating the first medication was taken, revising the first template signal based on the first motion signal segment or generating a third template signal based on the first motion signal segment,
    wherein the determination that the first medication was taken by the user is further based on the first response.

8. The method of claim 5, further comprising:
    obtaining a third user-specific template signal generated based on a motion signal segment sensed by the motion sensor while the user performed the first action,
    wherein the detection of the first action includes determining whether the first motion signal segment matches the third template signal.

9. The method of claim 5, further comprising:
    tracking positions of the user's left and right wrists using a camera and capturing motion signals sensed by the motion sensor while the user sequentially performs the first action at the first time and then the second action at the second time;

automatically determining a start and an end of the user's performance of the first action at the first time based on the tracked positions;

automatically determining a start and an end of the user's performance of the second action at the second time based on the tracked positions;

automatically identifying the third motion signal segment from the captured motion signals based on the determined start and end of the user's performance of the first action at the first time; and automatically identifying the fourth motion signal segment from the captured motion signals based on the determined start and end of the user's performance of the second action at the second time.

10. The method of claim 1, wherein the first action comprises the user opening a container containing the first medication; and the second action comprises the user moving a hand to the user's mouth.

11. The method of claim 10, wherein the container is a twist-cap prescription bottle, a foil wrapping, a syrup container, or a cream tube.

12. The method of claim 1, further comprising:

obtaining an indication that the user is in proximity to an RFID tag attached to a container containing the first medication, wherein the determination that the first medication was taken by the user is further based on the indication.

13. The method of claim 1, further comprising:

obtaining a proximity signal indicating that the user is in proximity to a container containing the first medication, the proximity signal including an identification of the container or a content of the container, wherein the determination that the first medication was taken by the user is further based on the proximity signal.

14. The method of claim 1, further comprising:

alerting the user with an audible or visible signal to take the first medication at a first time, wherein the determination that the first medication was taken by the user is further based on the first motion signal segment or the second motion signal segment having been sensed within a predetermined period of time after the first time.

15. The method of claim 1, further comprising:

obtaining a third motion signal segment sensed by the motion sensor, wherein the third motion signal segment was sensed by the motion sensor after the second motion signal segment;

detecting the user performed the first action based on the third motion signal segment;

obtaining a fourth motion signal segment sensed by the motion sensor, wherein the fourth motion signal segment was sensed by the motion sensor after the third motion signal segment;

detecting the user performed the second action based on the fourth motion signal segment; and issuing an alert in response to a time associated with the sensing of the fourth motion signal segment occurring within a predetermined amount of time of a time associated with the sensing of the second motion signal segment.

16. The method of claim 1, further comprising:

in response to the determination that the first medication was taken by the user, scheduling a reminder for the user to take the first medication.

17. A system for medication adherence monitoring, the system comprising:

a housing configured to be worn on a user's wrist or forearm;

a motion sensor mounted within the housing;

one or more processors each configured to execute instructions; and one or more nontransitory storage mediums configured to provide stored instructions to the one or more processors which cause the one or more processors to:

obtain a first motion signal segment sensed by the motion sensor;

detect the user performed a first action based on the first motion signal segment;

obtain a second motion signal segment sensed by the motion sensor, wherein the second motion signal segment was sensed by the motion sensor after the first motion signal segment;

detect the user performed a second action based on the second motion signal segment and in response to the detection of the first action;

determine that a first medication was taken by the user based on the detection of the second action; and cause presentation of an indication to the user or transmit an indication to an external device that the first medication was taken by the user in response to the determination that the first medication was taken by the user.

18. The system of claim 17, wherein the motion sensor includes an accelerometer configured with an axis for measuring acceleration that is substantially parallel to a longitudinal direction of the user's forearm when the housing is worn on the user's wrist or forearm.

19. The system of claim 17, wherein the one or more processors are mounted in the housing.

20. The system of claim 17, wherein the stored instructions further cause the one or more processors to:

identify a first segment of motion signals sensed by the motion sensor as the first motion signal segment in response to the first segment of motion signals matching a first user-specific template signal generated based on a third motion signal segment sensed by the motion sensor while the user performed the first action at a first time; and identify a second segment of motion signals sensed by the motion sensor as the second motion signal segment in response to the second segment of motion signals matching a second user-specific template signal generated based a fourth motion signal segment sensed by the motion sensor while the user performed the second action at a second time.

21. The system of claim 17, further comprising:

an RFID reader configured to generate a proximity signal indicating that the RFID reader is in proximity to an RFID tag attached to a container containing the first medication, wherein the stored instructions further cause the one or more processors to make the determination that the first medication was taken by the user further based on the proximity signal.

22. The system of claim 17, further comprising:

a proximity detector configured to generate a proximity signal in response to the proximity detector being in proximity to a container containing the first medication, the proximity signal including an identification of the container or a content of the container, wherein the stored instructions further cause the one or more processors to make the determination that the first medication was taken by the user further based on the proximity signal.

23. A nontransitory computer readable storage medium comprising a plurality of instructions which when executed by one or more processors, cause the one or more processors to:

obtain a first motion signal segment sensed by a motion sensor worn on a user's wrist or forearm;

detect the user performed a first action based on the first motion signal segment;

obtain a second motion signal segment sensed by the motion sensor, wherein the second motion signal segment was sensed by the motion sensor after the first motion signal segment;

detect the user performed a second action based on the second motion signal segment and in response to the detection of the first action;

determine that a first medication was taken by the user based on the detection of the second action; and in response to the determination that the first medication was taken by the user, cause presentation of an indication to the user or transmitting an indication to an external device that the first medication was taken by the user.

24. The nontransitory computer readable storage medium of claim 23, wherein the instructions further cause the one or more processors to:

initiate a time period to begin at a time associated with the sensing of the first motion signal segment, in response to the detection of the first action based on the first motion signal segment; and make the determination that the first medication was taken by the user further based on a time associated with the sensing of the second motion signal segment having occurred within a predetermined amount of time after the beginning of the time period.

25. The nontransitory computer readable storage medium of claim 23, wherein the instructions further cause the one or more processors to:

identify a first segment of motion signals sensed by the motion sensor as the first motion signal segment in response to the first segment of motion signals matching a first user-specific template signal generated based on a third motion signal segment sensed by the motion sensor while the user performed the first action at a first time; and identify a second segment of motion signals sensed by the motion sensor as the second motion signal segment in response to the second segment of motion signals matching a second user-specific template signal generated based a fourth motion signal segment sensed by the motion sensor while the user performed the second action at a second time.

26. The nontransitory computer readable storage medium of claim 23, wherein the instructions further cause the one or more processors to:

calculate a confidence level that the first motion signal segment matches the first template signal;

in response to the detection of the second action and the confidence level, cause presentation of a request for confirmation that the first medication was taken;

obtain a first response to the request indicating that the first medication was taken;

in response to the first response, revise the first template signal based on the first motion signal segment or generate a third template signal based on the first motion signal segment; and make the determination that the first medication was taken by the user further based on the first response.

27. The nontransitory computer readable storage medium of claim 23, wherein the instructions further cause the one or more processors to:

obtain an indication that the user is in proximity to an RFID tag attached to a container containing the first medication; and make the determination that the first medication was taken by the user further based on the indication.

28. The nontransitory computer readable storage medium of claim 23, wherein the instructions further cause the one or more processors to:

obtain a proximity signal indicating that the user is in proximity to a container containing the first medication, the proximity signal including an identification of the container or a content of the container; and make the determination that the first medication was taken by the user further based on the proximity signal.

* * * * *